(12) United States Patent
Dueva-Koganov et al.

(10) Patent No.: US 9,913,797 B2
(45) Date of Patent: Mar. 13, 2018

(54) BIOACTIVE COMPOSITIONS HAVING HAIR ANTI AGING ACTIVITY

(71) Applicant: ISP Investments Inc., Wilmington, DE (US)

(72) Inventors: Olga V. Dueva-Koganov, White Plains, NY (US); Michael Koganov, White Plains, NY (US); Jeanette Richards, Liberty Township, OH (US); Tom Dawson, Hamilton, OH (US); Mary Jane Combs, Covington, KY (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 14/366,845

(22) PCT Filed: Dec. 19, 2012

(86) PCT No.: PCT/EP2012/076131
§ 371 (c)(1),
(2) Date: Jun. 19, 2014

(87) PCT Pub. No.: WO2013/092698
PCT Pub. Date: Jun. 27, 2013

(65) Prior Publication Data
US 2014/0341829 A1    Nov. 20, 2014

Related U.S. Application Data

(60) Provisional application No. 61/579,155, filed on Dec. 22, 2011.

(51) Int. Cl.
*A61K 8/97* (2017.01)
*A61Q 5/00* (2006.01)
*A61Q 19/08* (2006.01)

(52) U.S. Cl.
CPC .................. *A61K 8/97* (2013.01); *A61Q 5/00* (2013.01); *A61Q 19/08* (2013.01); *A61K 2800/522* (2013.01); *A61K 2800/5922* (2013.01); *A61Q 5/002* (2013.01)

(58) Field of Classification Search
None
See application file for complete search history.

(56) References Cited

U.S. PATENT DOCUMENTS

| | | | |
|---|---|---|---|
| 2,809,971 A | 10/1957 | Bernstein et al. | |
| 3,236,733 A | 2/1966 | Karsten et al. | |
| 3,753,196 A | 8/1973 | Kurtz et al. | |
| 3,755,560 A | 8/1973 | Dickert et al. | |
| 3,761,418 A | 9/1973 | Parran et al. | |
| 4,323,683 A | 4/1982 | Bolich, Jr. et al. | |
| 4,345,080 A | 8/1982 | Bolich, Jr. | |
| 4,379,753 A | 4/1983 | Bolich, Jr. | |
| 4,421,769 A | 12/1983 | Dixon et al. | |
| 4,470,982 A | 9/1984 | Winkler | |
| 5,686,082 A | 11/1997 | N'Guyen | |
| 5,686,367 A | 11/1997 | Hayashi | |
| 7,473,435 B2 | 1/2009 | Koganov | |
| 7,537,791 B2 | 5/2009 | Koganov | |
| 2003/0175235 A1 | 9/2003 | Koganov | |
| 2004/0175347 A1 | 9/2004 | Bissett | |
| 2005/0048008 A1 | 3/2005 | Gupta | |
| 2005/0181079 A1 | 8/2005 | Koganov | |
| 2006/0275237 A1 | 12/2006 | Bissett et al. | |
| 2008/0064723 A1 | 3/2008 | Ideta et al. | |
| 2009/0123406 A1 | 5/2009 | Pheiffer | |
| 2010/0120871 A1 | 5/2010 | Dawson, Jr. et al. | |
| 2011/0110872 A1 | 5/2011 | Koganov et al. | |
| 2014/0348766 A1 | 11/2014 | Dueva-Koganov et al. | |

FOREIGN PATENT DOCUMENTS

| | | | |
|---|---|---|---|
| CN | 101559181 A | * | 10/2009 |
| DE | 41 18 098 C1 | | 5/1992 |
| EP | 1 262 167 A1 | | 12/2002 |
| EP | 1 543 822 A1 | | 6/2005 |
| EP | 1 543 823 A1 | | 6/2005 |
| EP | 1 806 121 A1 | | 7/2007 |
| FR | 2 946 886 A1 | | 12/2010 |
| JP | 2002-020243 A | | 1/2002 |
| JP | 2002-332240 A | | 11/2002 |
| JP | 2005-296352 A | | 10/2005 |
| JP | 2006-008536 A | | 1/2006 |
| JP | 2008-137998 A | | 6/2008 |
| KR | 10-2009-0009559 A | | 1/2009 |
| WO | 02/074280 A1 | | 9/2002 |
| WO | 2007/098471 A2 | | 8/2007 |
| WO | 2010/054343 A2 | | 5/2010 |

OTHER PUBLICATIONS

Notification of Transmittal of the International Search Report and the Written Opinion of the International Searching Authority, or the Declaration from the International Bureau of WIPO for International Application No. PCT/EP2012/076131 dated Nov. 15, 2013.
McCutcheon, Emulsifiers & Detergents, North American Edition, pp. 317-324 (1986).
Morioka et al, "Effects of Zinc on the New Preparation Method of Hydroxy Double Salts," Inorganic Chemistry, vol. 38, No. 19, pp. 4211-4216 (1999).
Crepaldi et al., "Chemical, Structural, and Thermal Properties of Zn(II)-Cr(III) Layered Double Hydroxides Intercalated with Sulfated and Sulfonated Surfactants," Journal of Colloid and Interface Science 248, pp. 429-442 (2002).
"Cosmetic material for conditioning skin and hair—comprises compounded Japanese parsley extracts with extracts of specific Rosaceae plants," WPI Wolrd Patent Information Derwent, vol. 26, No. 88, May 20, 1988, XP002041404, abstract.

* cited by examiner

*Primary Examiner* — Amy L Clark
(74) *Attorney, Agent, or Firm* — FisherBroyles, LLP; William J. Davis

(57) ABSTRACT

A bioactive composition and method of using the composition is provided having anti-aging, antioxidant and/or free radical scavenging properties.

9 Claims, 7 Drawing Sheets

| Serum Fraction/Blend | Lot # | Dry wt | pH | Blend Preparation (serum fraction parts added) |
|---|---|---|---|---|
| Kelp | 0320J/MS-0363 | 4.80% | 5 | N/A |
| Kelp | 0320J/MS-0492 | 4.70% | 4.7 | N/A |
| Kelp | 0320J/MS-0492-01 | 4.70% | 4.7 | N/A |
| Kelp | MP0726M/MS-0571 | 4.70% | 5.1 | N/A |
| Parsley | PA1117L/HP-0499 | 4.50% | 3.9 | N/A |
| Parsley | PA1117L/HP-0570 | 4.50% | 4.1 | N/A |
| Kelp-Parsley 10:90 | B19-0729M/OS-0572 | 4.30% | 4.1 | 1 Part Kelp + 9 Parts Parsley |
| Kelp-Parsley 20:80 | B19-0729M/OS-0573 | 4.30% | 4.1 | 2 Parts Kelp + 8 Parts Parsley |
| Kelp-Parsley 30:70 | B19-0729M/OS-0574 | 4.30% | 4.1 | 3 Parts Kelp + 7 Parts Parsley |
| Kelp-Parsley 40:60 | B19-0729M/OS-0575 | 4.30% | 4.1 | 4 Parts Kelp + 6 Parts Parsley |
| Kelp-Parsley 50:50 | B19-0215M/OS-0529 | 4.50% | 4 | 1 Part Kelp +1 Part Parsley |
| Kelp-Parsley 50:50 | B19-0712M/OS-0563 | 4.50% | 4 | 1 Part Kelp +1 Part Parsley |
| Kelp-Parsley 50:50 | B19-0729M/OS-0576 | 4.30% | 4.2 | 5 Parts Kelp + 5 Parts Parsley |
| Kelp-Parsley 60:40 | B19-0729M/OS-0577 | 4.50% | 4.3 | 6 Parts Kelp + 4 Parts Parsley |
| Kelp-Parsley 70:30 | B19-0729M/OS-0578 | 4.40% | 4.3 | 7 Parts Kelp + 3 Parts Parsley |
| Kelp-Parsley 80:20 | B19-0729M/OS-0579 | 4.40% | 4.5 | 8 Parts Kelp + 2 Parts Parsley |
| Kelp-Parsley 90:10 | B19-0729M/OS-0580 | 4.50% | 4.7 | 9 Parts Kelp + 1 Part Parsley |
| Camellia | TECJ062904-0184 | 8.10% | 4 | N/A |
| Camellia | TECJ062904-0184-01 | 8.10% | 4.1 | N/A |
| Camellia | TECJ062904-0161-01 | 7.50% | 4.1 | N/A |
| Camellia | TECJ062904-0554 | 7.40% | 4.2 | N/A |
| Feverfew | FF0811K/TL | 8.20% | 3.9 | N/A |
| Camellia-Feverfew 20:80 | FFCSWASC02P-0351 | 7.60% | 3.8 | 2 Parts Camellia + 8 Parts Feverfew |
| Camellia-Feverfew 20:80 | FFCSWASC02P-0351-01 | 7.60% | 3.9 | 2 Parts Camellia + 8 Parts Feverfew |
| Camellia-Feverfew 20:80 | B02-0712M/OS-0562 | 7.50% | 3.4 | 1 Part Camellia + 4 Parts Feverfew |
| Camellia-Feverfew 50:50 | B02-0712M/OS-0561 | 7.50% | 3.6 | 1 Part Camellia + 1 Part Feverfew |
| Camellia-Feverfew 80:20 | B02-0719M/OS-0567 | 7.50% | 4.1 | 4 Parts Camellia + 1 Part Feverfew |

FIG. 7

BIOACTIVE COMPOSITIONS HAVING HAIR ANTI AGING ACTIVITY

FIELD OF THE INVENTION

The present invention relates to hair care compositions and methods that can increase the appearance of thicker and/or fuller hair and/or delay the appearance of gray hair to provide healthy and younger looking hair.

BACKGROUND OF THE INVENTION

Many attributes contribute to the appearance of hair considered to be attractive. For instance, hair with a full and thick appearance is very desirable. In contrast, hair with a thin appearance is not as attractive, and can even lead to a perception that the thin-haired individual is older than their chronological age. Additionally, the appearance of gray hair can also lead to the perception that an individual is older than their chronological age. Furthermore, thin hair and gray hair can be more difficult to style, and typically cannot be styled into as many hairstyles, leaving the individual frustrated and with an unkempt appearance. Because of the foregoing problems associated with thin hair and graying hair, many individuals expend great effort and time on grooming, yet still do not attain their desired hairstyle and appearance. This can lead to frustration and/or lack of confidence in his or her appearance. These problems can be experienced by both female and male consumers and at a variety of ages.

Accordingly, there is a need to provide consumers with a way to increase the fullness and thickness of hair appearance and reduce the appearance of gray hair, thus resulting in healthier and younger-looking, more attractive hair appearance.

SUMMARY OF THE INVENTION

The present invention relates to hair care compositions and methods that can help increase the appearance of fuller and/or thicker hair and/or reduce the appearance of gray hair, thus resulting in healthier and younger-looking hair. This result is achieved by increasing the diameter of hair shafts and follicles, increasing the number of hairs, reducing the emergence of gray hairs, and/or having hair with less damage.

According to one aspect of the present invention, a hair care composition is provided that comprises an effective amount of a synergistic combination of hair anti-aging agents to the scalp for the purpose of improving the appearance of the hair by providing healthy and younger looking mammalian hair. The composition comprises an effective amount of hair anti-aging agents selected from a first composition comprising a combination of *camellia* serum fraction and a feverfew serum fraction, or a second composition comprising a combination of a parsley serum fraction and a kelp serum fraction; and a dermatologically acceptable carrier.

According to one aspect of the present invention, a method is provided that comprises topically applying the hair care composition comprising an effective amount of a synergistic combination of hair anti-aging agents to the scalp for the purpose of improving the appearance of the hair.

BRIEF DESCRIPTION OF THE DRAWINGS

It is believed that the present invention will be better understood from the following description taken in conjunction with the accompanying drawings. The referenced drawings are not to be construed as limiting the scope of the present invention.

FIG. 7 is a table showing the identity of the serum fractions and blends used herein.

DETAILED DESCRIPTION OF THE INVENTION

Figure 1:
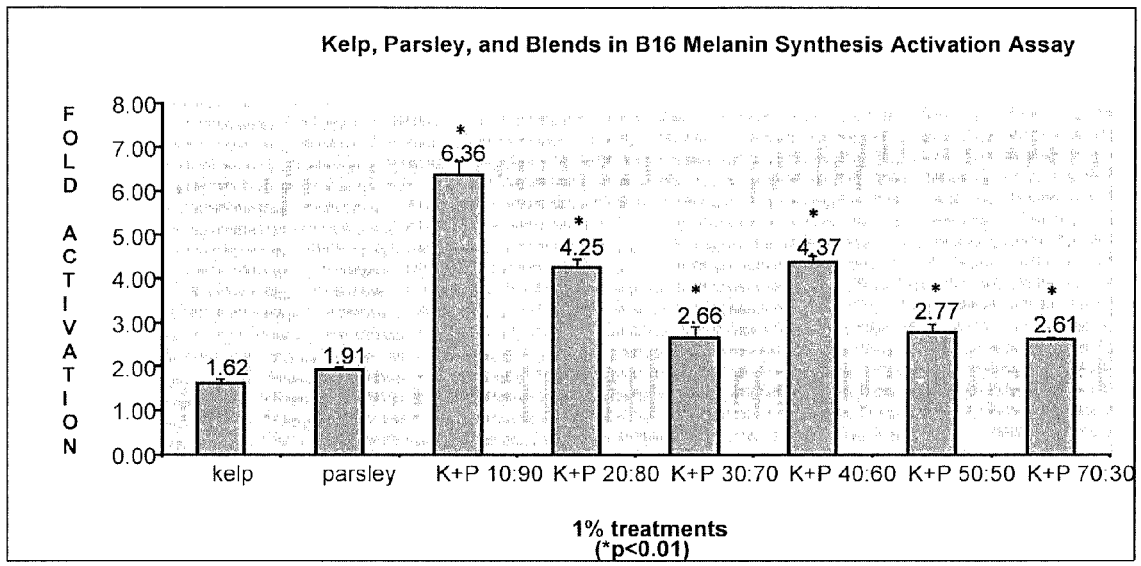
FIG. 1 is a bar graph showing melanin synthesis activation when kelp and parsley serum fractions are evaluated separately and as varied blends in a melanocyte assay.
Figure 2:
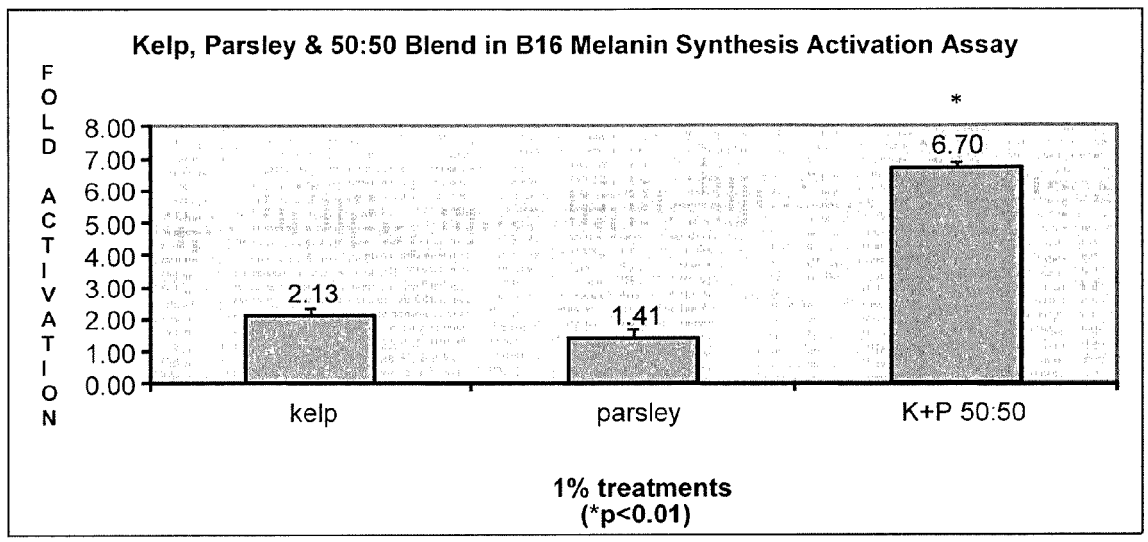
FIG. 2 is another bar graph showing melanin synthesis activation when kelp and parsley serum fractions are evaluated separately and as a 50:50 blend in a melanocyte assay.
Figure 3:
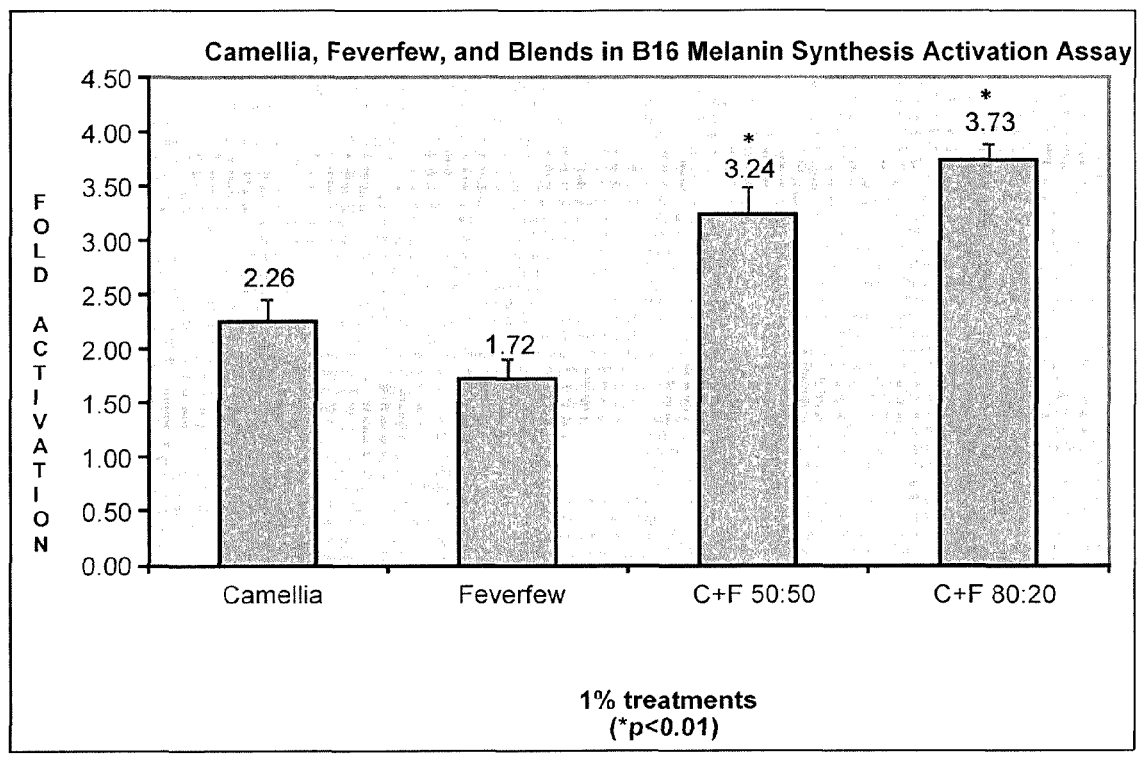
FIG. 3 is a bar graph showing melanin synthesis activation when *camellia* and feverfew serum fractions are evaluated separately and as varied blends in a melanocyte assay.
Figure 4:
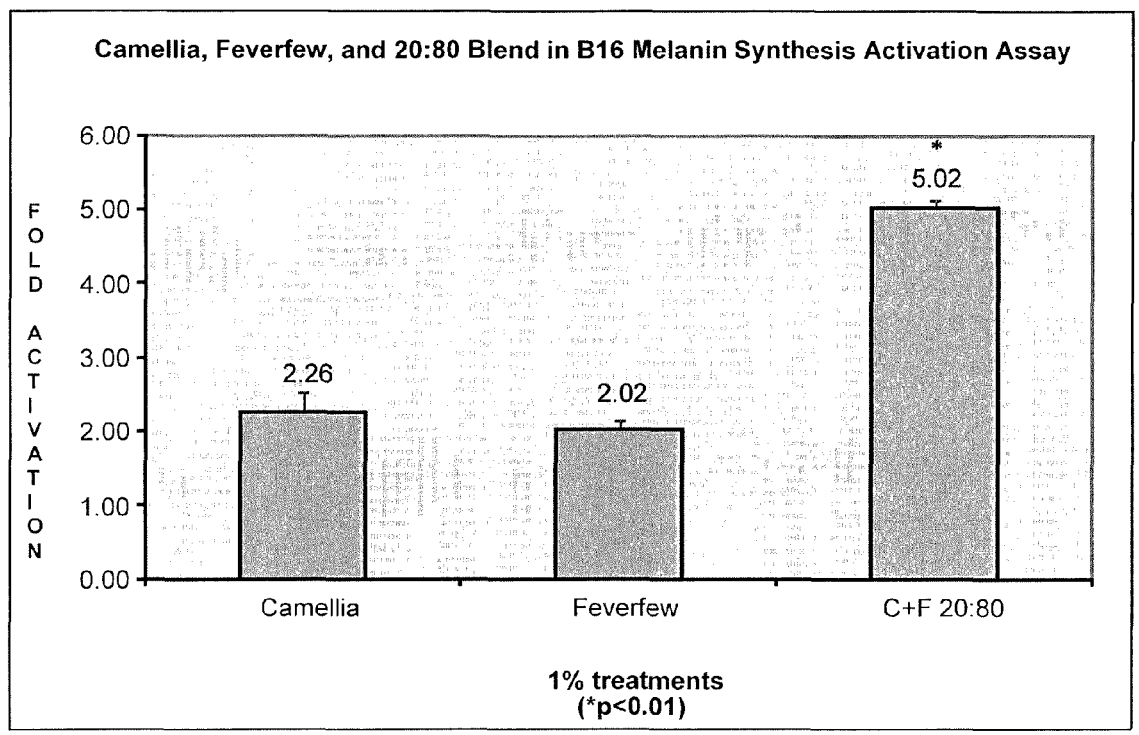
FIG. 4 is another bar graph showing melanin synthesis activation when *camellia* and feverfew serum fractions are evaluated separately and as 20:80 blend in a melanocyte assay.
Figure 5:
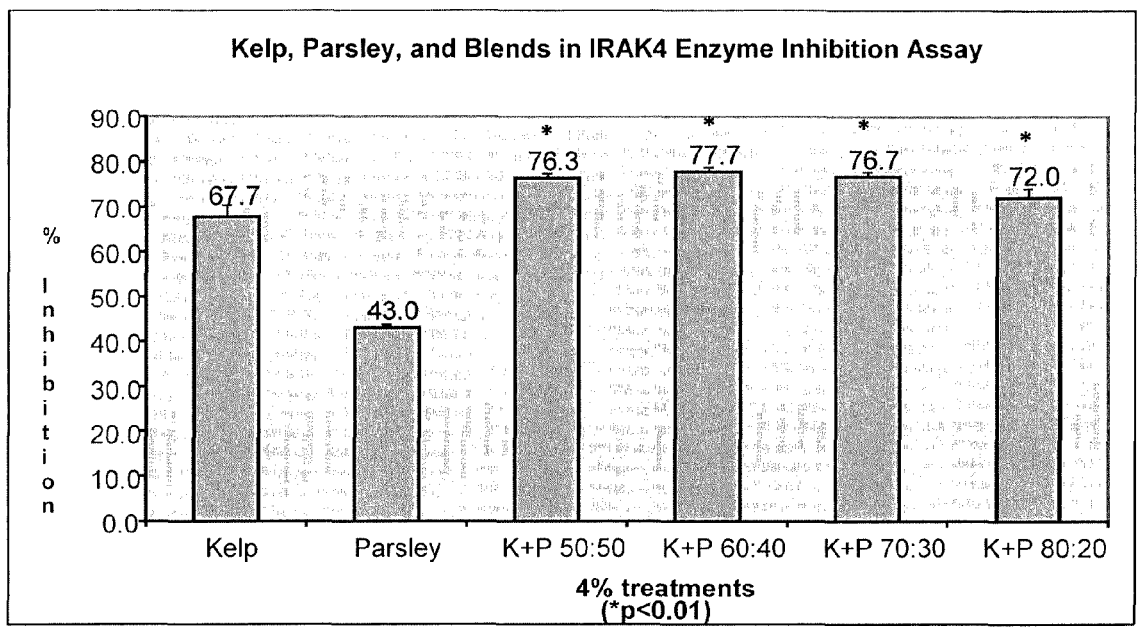
FIG. 5 is a bar graph showing inhibition of interleukin-1 receptor-associated kinase (IRAK-4) when kelp and parsley serum fractions are evaluated separately and as varied blends in an ADP-Glo™ assay.
Figure 6:
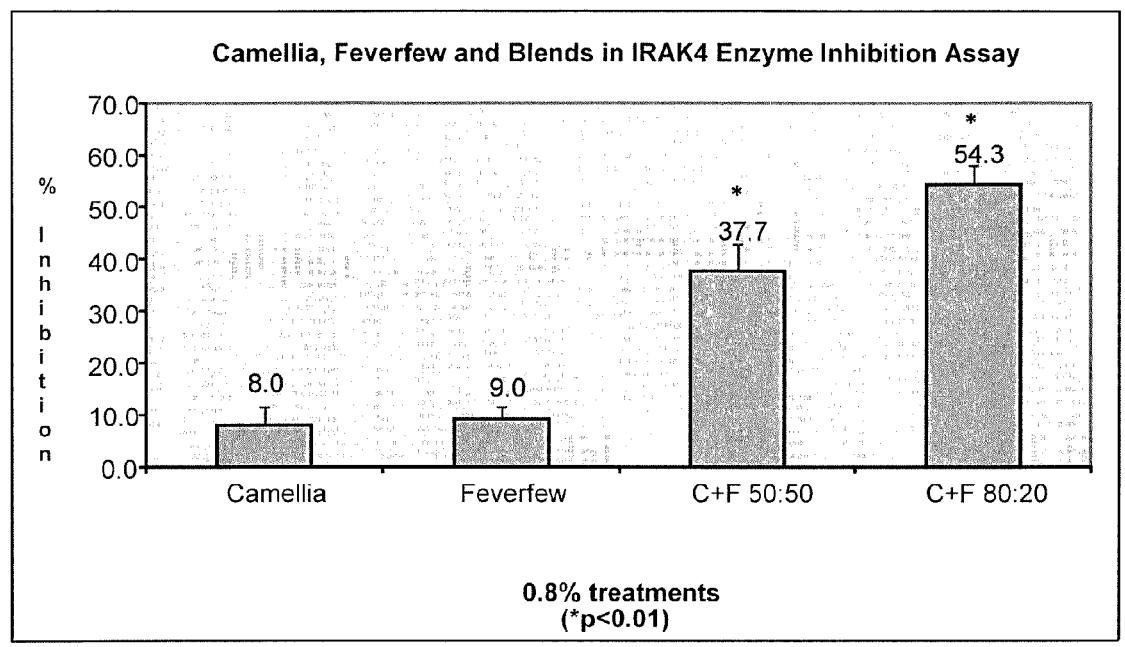
FIG. 6 is a bar graph showing inhibition of IRAK-4 when *camellia* and feverfew serum fractions are evaluated separately and as varied blends in an ADP-Glo™ assay.

As used herein, the term "hair care compositions" are compositions that are applied to the hair and/or the skin underneath the hair, including compositions used to treat or care for the hair. Products contemplated by the phrase "hair care composition" include, but are not limited to after-shave tonics and lotions, creams, emulsions, foams, hair conditioners (rinse-off and leave-on), hair colorants, hair tonics, liquids, lotions, mousses, propellant lotions, shampoos, shave gels, temporary beard hair dyes, and the like.

"Hair growth stimulating agent" includes any material that can increase or extend an anagen phase, or provide the appearance of increasing the anagen phase of mammalian hair growth, when an effective amount of a composition containing a hair growth stimulating agent is topically applied to the desired region over a result-effective period of time. All relative terms used in connection with hair growth stimulation are understood to mean that the benefit observed is relative to that which is observed or would be expected without the exposure of a composition described herein. These observations include, but are not limited to increasing the diameter of hair shafts and follicles, increasing the number of hairs, growing longer hair, and/or having hair with less damage.

"Increase the appearance of fuller and thicker hair" means the diameters of hair follicles and/or shafts in the subject region of hair (e.g., scalp) are increased by a statistically significant amount, when an effective amount of a composition of the present invention is topically applied to the desired region over a result-effective period of time.

"Delay the appearance of gray hair" means the rate of gray hair emerging is delayed. It is accepted that canities (i.e., natural whitening or graying of the hair) is associated with a decrease in melanin in the hair shaft. The onset or degree of canities is associated with aging, and thus the delaying the onset of or decreasing the appearance of gray hair provides a younger looking appearance. The rate of gray hair emergence can be measured by visual observation and by the method described in Japanese patent application 2005-296352A and U.S. Patent Application Publication No. 2008/0064723, both of which are assigned to Shiseido Company, LTD. The counting method consists of designating a 50 mm×10 mm area on either side of the frontal scalp and collecting all the hairs within the area and counting 1000 hairs cut from the area. Gray hairs and pigmented hairs are both counted. The process is repeated monthly, or as desired, and the percent of gray hairs is calculated.

"Mammalian hair," as referenced herein, includes hair on any part of the body of a mammal, and can include but is not limited to facial, cranial, or body hair. For instance, it can include hair on the scalp, head, neck, beard, moustache, eyebrows and sideburns hair.

The term "topical application," as used herein, means to apply or spread the compositions of the present invention onto the surface of the keratinous tissue from which the hair to be affected grows.

The term "dermatologically-acceptable," as used herein, means that the compositions or components thereof so described are suitable for use in contact with mammalian keratinous tissue without undue toxicity, incompatibility, instability, allergic response, and the like.

The term "effective amount," as used herein, means an amount of a compound or composition sufficient to increase the diameter of the shafts in the subject region of hair by a statistically significant amount, to increase the hair density (number of hairs per area) by a statistically significant amount, and/or to delay the appearance of gray hair by a statistically significant amount.

The term "serum fraction," as used herein, means a composition produced by a general method comprising the steps of: (a) grinding and pressing of clean, fresh, plant matter and (b) separating a liquid fraction from a cell wall fraction to obtain fresh cell juice, wherein no exogenous liquid is added prior or during said separating; (c) filtering the fresh cell juice to obtain a first filtrate; and (d) fractionating the first filtrate to obtain the serum fraction.

I. Hair Care Compositions

The present invention relates to hair care compositions, and methods of using the compositions, that are useful for application to a scalp surface and comprise an effective amount of hair anti-aging agents, which are effective for providing younger looking hair. The compositions may be in a wide variety of product forms that include, but are not limited to, solutions, suspensions, lotions, creams, gels, toners, sticks, pencil, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, and the like. The composition form may follow from the particular dermatologically acceptable carrier chosen, if present in the composition.

A. Hair Anti-Aging Agents

The hair care compositions in accordance to embodiments of the present invention comprise an effective amount of a combination of hair anti-aging agents which are serum fractions. Accordingly, in an embodiment, the hair care composition comprises a first combination of a *camellia* serum fraction and a feverfew serum fraction; or a second combination of a parsley serum fraction and a kelp serum fraction. According to another embodiment the hair care composition comprises the first and the second combinations.

The *camellia*, feverfew, or parsley fractions each consist essentially of the flower, leaf, and/or stem serum fractions obtained from plants belonging to *camellia sinensis, chrysanthemum parthenium,* or *petroselinum crispum,* respectively, and the kelp serum fraction consists essentially of a bioactive fraction from a photosynthetic organism *macrocystis pyrifera*, which is commonly known as brown algae. For purposes of simplifying the discussion herein, brown algae should be understood to be inclusive to "plant" or "plants" or "biomass" when referencing the source of a serum fraction. Exemplary serum fractions used herein are provided by Akzo Nobel Surface Chemistry LLC, Chicago, Ill. Exemplary serum fraction preparation methods are set forth in U.S. Pat. No. 7,473,435 (e.g., for *camellia*), U.S. Pat. No. 7,537,791 (e.g., for parthenolide free bioactive ingredients from feverfew (*Tanacetum parthenium*)), and U.S. Patent Application Publication No. 2011/0110872 (e.g., for kelp), which are incorporated herein by reference in their entirety. The serum fractions may be blended to form a combination of serum fractions that surprisingly produce synergistic effects, as discussed further below.

The general method for preparing a serum fraction comprises the steps of: grinding and pressing of clean, fresh plant matter; separating a liquid fraction from a cell wall fraction to obtain fresh cell juice, wherein no exogenous liquid is added prior or during said separating; filtering the fresh cell juice to obtain a first filtrate; and fractionating the first filtrate to obtain the serum fraction for use herein. Fractionating may include one or more of the following steps: adjusting pH, heating such as microwaving, filtering, centrifuging, or stabilizing. Stabilizing may include adding preservatives and incubating the mixture until complete solubilization of the preservative is achieved. Exemplary preservatives include one or more of potassium sorbate, sodium benzoate, sodium methyl paraben, and/or citric acid.

The resulting combinations of serum fractions have superior bioactivity versus traditionally prepared plant extracts. Unlike traditional extracts, the serum fraction is prepared from fresh plant cell juice that has been mechanically separated from the rest of the fresh plant material. Importantly, no exogenous solvent (e.g., water, hexane, acetone, ethanol) is added during the juice separation process. The resulting cell juice contains the full spectrum of compounds found in fresh plant matter, thus the resulting serum fractions contain a much broader range of active compounds than do traditional plant extracts, which contain only the narrow range of compounds that can be separated with a particular solvent.

Furthermore, using fresh plants maintains the integrity of the bioactive components inherently present in the fresh plant matter. Traditional plant extracts are not prepared from fresh plant matter, but rather from dried plant material, which has undergone degradation due to dehydration. During dehydration, the cell walls are compromised, causing the degradation of compounds through mechanisms such as hydrolysis, oxidation, polymerization, Maillard reactions, and isomerization. When the dried leaves are extracted, the resulting extract thus contains these degradation products that were not originally present in the fresh plant matter. Accordingly, the composition of the resulting dry leaf extract greatly differs from that of fresh juice and the resulting serum fraction.

An exemplary preparation of a *camellia sinensis* serum fraction is described in U.S. Pat. No. 7,473,435, and is summarized below. The serum fraction from *camellia sinensis* plants can be prepared by a method comprising the steps of (1) biomass preparation; (2) grinding, maceration, and pressing of plant biomass; (3) separation of a membrane fraction from the cell juice to provide a cell juice supernatant; (4) separation of a cytoplasm fraction from the cell juice supernatant; and (5) isolation of the serum fraction.

(1) Biomass Preparation: Sufficient amounts of fresh *camellia (camellia sinensis)* plant biomass (only top tender young leaf tissue with buds) are harvested to yield approximately 100 kg of dry matter. The level of dry matter in the fresh biomass is calculated to be 21.70 wt %, requiring harvesting of approximately 461 kg of fresh plant biomass to yield 100 kg of dry matter. Care is taken to preserve the inherent moisture content of the plant biomass and to avoid wilting due to moisture loss. The harvesting is conducted in such a manner as to avoid or minimize chopping, mashing, and crushing of the collected biomass to avoid the disruption of the leaf cell structure, which can induce endogenous enzymatic reactions catalyzed by phenol-oxidase and peroxidase. Because these reactions are intensified with the time of oxidation, all steps are completed in the shortest possible period of time. For example, the harvested biomass is delivered for processing not more than 10 minutes after cutting. This is done to minimize exposure of the plant biomass to sun, high temperature, and other negative environmental factors. A washing step is performed to remove soil particles and other debris from the plants prior to further processing. This washing is accomplished by washing the harvested plants for ≤5 minutes in ≤1 kg/cm$^2$ water pressure. The residual water wash does not contain any green or brown pigments, indicating proper water pressure and washing duration. The excess water is removed from the washed plant biomass.

(2) Grinding, Maceration, and Pressing of Plant Biomass: After harvesting, collecting, and washing the plant biomass, the plants then undergo grinding, maceration, and pressing to extract the intracellular content (i.e., the plant cell juice) and to separate the plant cell juice from the fiber-enriched cell walls fraction (cell walls fraction). A hammer mill (Model VS 35, Vincent Corporation, Fla.) having 10 HP engine and set of screens may be used to grind the biomass to yield plant tissue particles of suitably small size in a shortest amount of time and without significant increase of biomass temperature. The hammer mill can be set to produce the maximum size of macerated plant particles of ≤0.5 centimeters during ≤10 seconds of treatment. The biomass temperature is increased only ≤5° C. A horizontal continuous screw press (Compact Press "CP-6", Vincent Corporation, Fla.) is immediately used to extract the plant cell juice from the plant. The pressure on the cone of the screw press is maintained at a level of 24 kg/cm$^2$, with a screw speed of 12 rpm and only a temperature increase of ≤5° C. This treatment can yield about 276 kg of plant cell juice having dry mater level of about 8.5 wt %.

(3) Separation of the Membrane Fraction from the Cell Juice: The initial plant cell juice having dry matter level of about 8.5 wt % contains small fiber particles, which can be removed by filtration through four layers of nylon fabric or by using low-speed centrifugation biomass. The filtered plant cell juice is exposed to microwave treatment using a temperature probe control. This treatment continues until the temperature of the cell juice reached 60° C. Once coagulation is induced, the treated cell juice is immediately cooled to 40° C. Separation of the membrane fraction from the coagulated cell juice is achieved using centrifugation at greater than or equal to 3,000 g for greater than or equal to 20 minutes. This yields a membrane fraction (precipitate) and a cell juice supernatant, which contains a cytoplasm fraction and a cell serum fraction (which contains low molecular weight soluble components). The cell juice supernatant is used for further processing to yield a serum fraction.

(4) Separation of the Cytoplasm Fraction from the Cell Juice Supernatant: In order to separate out the cytoplasm fraction, the cell juice supernatant is subjected to isoelectric precipitation. Precipitation of the cytoplasm fraction is induced using a titration method utilizing 5.0 N Hydrochloric Acid (HCl) to bring the pH of the cell juice supernatant to about 4. The separation of precipitated cytoplasm fraction, which may have a dry matter level of about 14.5 wt %, from supernatant is achieved by centrifugation at greater than or equal to 3,000 g (where g is the relative centrifugal force) for greater than or equal to 20 minutes.

(5) Isolation of the Serum Fraction: After separation of the cytoplasm fraction, the supernatant contains suspended particles. In order to separate out these particles, the supernatant is centrifuged at greater than or equal to 7,500 g for greater than or equal to 30 minutes. The transparent supernatant is filtered through a filter having 0.8 micrometer pores. This filtrate (*camellia sinensis* serum fraction) can have a dry matter level of about 5.7 wt %.

It can be appreciated that the dry matter level of the serum fraction can vary depending on a variety of factors such as the moisture content of the plant biomass, which itself may have variations based on seasonal and/or geographical source. Accordingly, in one embodiment the dry matter level in the *camellia* serum fraction can range from about 0.1 wt % to about 25 wt %, from about 1 wt % to about 15 wt %, from about 2 wt % to about 10 wt %, or from about 3 wt % to about 9 wt %, for example. In one embodiment, the dry matter level in the feverfew fraction can range from about 0.1 wt % to about 25 wt %, from about 1 wt % to about 15 wt %, from about 2 wt % to about 10 wt %, or from about 3 wt % to about 9 wt %, for example. In one embodiment, the dry matter level in the kelp fraction can range from about 0.1 wt % to about 25 wt %, from about 1 wt % to about 15 wt %, from about 2 wt % to about 10 wt %, or from about 3 wt % to about 9 wt %, for example. In one embodiment, the dry matter level in the parsley fraction can range from about 0.1 wt % to about 25 wt %, from about 1 wt % to about 15 wt %, from about 2 wt % to about 10 wt %, or from about 3 wt % to about 9 wt %, for example. In another embodiment, the dry matter level in the blend of the kelp and parsley serum fractions and/or the *camellia* and feverfew serum fractions can range from about 0.1 wt % to about 25 wt %, from about 1 wt % to about 15 wt %, from about 2 wt % to about 10 wt %, or from about 3 wt % to about 9 wt %, for example.

Furthermore, the serum fractions can be further characterized with respect to the content of specified compounds or classes of compounds in the serum fraction and/or the dry matter, or by the absence of other compounds or class of compounds. For example, in one embodiment, the *camellia* serum fraction can have a total catechin content of between about 8.0 and about 20.0 milligrams per gram of dry matter, particularly between about 10.0 and about 18.0 milligrams per gram of dry matter, and more particularly between about 12.0 and about 16.0 milligrams per gram of dry matter. In another example, the feverfew serum fraction is either free of, or substantially free of, α-unsaturated γ-lactones, such as parthenolide.

Similar, analysis and characterization can applied to the feverfew (see e.g., U.S. Pat. No. 7,537,791), kelp (see e.g., U.S. Patent Application Publication No. 2011/0110872), and parsley serum fractions.

In some instances, a serum fraction cannot be used as an active ingredient of topical products due to a lack of stability and deterioration of color and odor. A refinement of the serum fraction may involve the following steps: heat treatment, cooling, filtration, and stabilization. Refinement can be performed immediately after separation of the serum fraction from the cytoplasm fraction. For example, the *camellia* serum fraction is exposed to microwave treatment using a temperature probe control. This treatment continues until the temperature of the serum fraction reaches 99° C. (90° C. is required as was previously described in U.S. Pat. No. 7,537,791, which is hereby incorporated by reference in its entirety). Once coagulation is induced, the treated serum fraction is immediately cooled to 10° C. The coagulated serum fraction is vacuum filtrated through filter having porous 0.8 micrometer (double layers of Whatman No. 2 filters may also be used as described in U.S. Pat. No. 7,537,791). The precipitate may be discarded and the resulting serum fraction filtrate can undergo further processing for stabilization. Stabilization of the serum fraction filtrate is achieved by adding preservatives (no exogenous anti-oxidant is required as was previously described in U.S. Pat. No. 7,537,791) and incubating the mixture until complete solubilization is achieved. The preservatives useful for stabilization of the serum fraction filtrate include the following: 0.1% potassium sorbate, 0.1% sodium benzoate, 0.1% sodium methyl paraben, and/or 0.1% citric acid. The recommended storage conditions for the *camellia* serum fraction includes storage in a closed container protected from light at a temperature of between 15° C. and 25° C.

Similar processing of *chrysanthemum parthenium, petroselinum crispum*, or *macrocystis pyrifera* can yield the serum fractions of feverfew, parsley, or kelp, respectively.

In some embodiments, the hair care composition comprises an effective amount of hair anti-aging agents that comprises a first combination of a *camellia* serum fraction and a feverfew serum fraction, the *camellia* serum fraction being present in an amount of from about 0.001 wt % to about 15 wt %, alternatively from about 0.002 wt % to about 10 wt %, alternately from about 0.025 wt % to about 10 wt %, in other embodiments from about 0.05 wt % to about 10 wt %, in others from about 0.05 wt % to about 5 wt %, and in others from about 0.1 wt % to about 5 wt %; and the feverfew serum fraction being present in an amount from about 0.001 wt % to about 15 wt %, from about 0.002 wt % to about 10 wt %, from about 0.025 wt % to about 10 wt %, from about 0.05 wt % to about 10 wt %, from about 0.05 wt % to about 5 wt %, or from about 0.1 wt % to about 5 wt %, wherein the wt % is based on the weight of the hair care composition.

According to another embodiment, weight ratio of the *camellia* serum fraction to the feverfew serum fraction ranges from about 10:90 to about 90:10, from about 10:90 to about 50:50; from about 80:20 to about 20:80, from about 30:70 to about 70:30, from about 40:60 to about 60:40. For example, the weight ratio of the *camellia* serum fraction to feverfew serum fraction may be about 90:10, about 80:20, about 70:30, about 60:40, about 50:50, about 40:60, about 30:70, about 20:80, or about 10:90.

In another embodiment, the hair care composition comprises an effective amount of a second combination of hair anti-aging agents that comprises a parsley serum fraction and a kelp serum fraction, the parsley serum fraction being present in an amount from about 0.001 wt % to about 15 wt %, from about 0.002 wt % to about 10 wt %, from about 0.025 wt % to about 10 wt %, from about 0.05 wt % to about 10 wt %, from about 0.05 wt % to about 5 wt %, or from about 0.1 wt % to about 5 wt %; and the kelp serum fraction being present in an amount from about 0.001 wt % to about 15 wt %, from about 0.002 wt % to about 10 wt %, from about 0.025 wt % to about 10 wt %, from about 0.05 wt % to about 10 wt %, from about 0.05 wt % to about 5 wt %, or from about 0.1 wt % to about 5 wt %, wherein the wt % is based on the weight of the hair care composition.

According to another embodiment, weight ratio of the parsley serum fraction to the kelp serum fraction ranges from about 10:90 to about 90:10, from about 10:90 to about 50:50; from about 80:20 to about 20:80, from about 30:70 to about 70:30, from about 40:60 to about 60:40. For example, the weight ratio of the parsley serum fraction to kelp serum fraction may be about 90:10, about 80:20, about 70:30, about 60:40, about 50:50, about 40:60, about 30:70, about 20:80, or about 10:90.

B. Dermatologically Acceptable Carrier

The compositions of the present invention may also comprise a dermatologically acceptable carrier (which may be referred to as "carrier") for the composition. The phrase "dermatologically acceptable carrier", as used herein, means that the carrier is suitable for topical application to the keratinous tissue, has good aesthetic properties, is compatible with the hair anti-aging agents in the composition, and will not cause any unreasonable safety or toxicity concerns. A suitable carrier is selected to yield a desired product form. Furthermore, the solubility or dispersibility of the components may dictate the form and character of the carrier. In one embodiment, the carrier is present at a level of from about 50 wt % to about 99 wt %, about 60 wt % to about 98 wt %, about 70 wt % to about 98 wt %, or, alternatively, from about 80 wt % to about 95 wt %, by weight of the composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

The aqueous phase comprises water, such as demineralized or distilled water, for example. Other acceptable carriers that may be used in the aqueous carrier include, but are not limited to alcohol compounds, such as ethanol. According to one embodiment, the composition comprises alcohol, dipropylene glycol, and/or water.

The hair care compositions have a pH ranging from about 3.0 to about 10, which may be measured by taking a direct pH measurement using a standard hydrogen electrode of the composition at 25° C. Accordingly, the pH of the hair care composition may be within the range from about 6 to about 9, for example.

Emulsions may further comprise an emulsifier. The composition may comprise any suitable percentage of emulsifier to sufficiently emulsify the carrier. Suitable weight ranges include from about 0.1 wt % to about 10 wt % or about 0.2 wt % to about 5 wt % of an emulsifier, based on the weight of the composition. Emulsifiers may be nonionic, anionic or cationic. Suitable emulsifiers are disclosed in, for example, U.S. Pat. Nos. 3,755,560, 4,421,769, and *McCutcheon's Detergents and Emulsifiers*, North American Edition, pages 317-324 (1986), which are incorporated herein by reference in their entirety. Suitable emulsions may have a wide range of viscosities, depending on the desired product form.

C. Optional Ingredients

According to embodiments of the present invention, the hair care compositions can also additionally comprise suitable optional ingredients as desired. For example, the composition can optionally include other active or inactive ingredients.

According to yet another embodiment, the hair care composition may further include one or more additional hair anti-aging agents, such as those disclosed in U.S. Patent Application Publication No. 2010/0120871, which is incorporated herein by reference in its entirety. Accordingly, non-limiting examples of additional hair growth stimulating agents include flavonoids such as apigenin and luteolin, indole compounds, xanthine compounds, vitamin $B_3$ compounds, panthenol compounds, and derivatives thereof.

1. Flavonoids

The compositions of embodiments of the present invention may optionally contain a flavonoid compound. Flavonoids are broadly disclosed in U.S. Pat. Nos. 5,686,082 and 5,686,367, both of which are herein incorporated by reference. Flavonoids suitable for use in embodiments of the present invention are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1-C8 alkyl, C1-C4 alkoxyl, 0-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2', 4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy iso flavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

In an embodiment, the flavonoid compound is an unsubstituted flavanone, methoxy flavanones, unsubstituted chalcone, 2',4-dihydroxy chalcone, and mixtures thereof. For example, in another embodiment, are unsubstituted flavanone, unsubstituted chalcone (e.g., the trans isomer), and mixtures thereof.

Flavonoids can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

When included in the hair care composition, the herein described flavonoid compounds can be present at concentrations of from about 0.01 wt % to about 20 wt %, of from about 0.1 wt % to about 10 wt %, or from about 0.5 wt % to about 5 wt %, wherein the wt % is based on the total weight of the hair care composition.

2. Indole Compounds

The hair care compositions can further include an indole compound. As used herein, "indole compound" means one or more indoles, derivatives thereof, mixtures thereof, or salts thereof. Accordingly, the composition may include from about 0.1 wt % to about 10 wt % of the indole compound, from about 0.5 wt % to about 5 wt % of the indole compound, or from about 1 wt % to about 2 wt % of the indole compound, for example, wherein the wt % is based on the total weight of the hair care composition.

3. Xanthine Compounds

The hair care compositions can further include a xanthine compound. As used herein, "xanthine compound" means one or more xanthines, derivatives thereof, and mixtures thereof. Xanthine compounds that can be useful herein include, but are not limited to, caffeine, xanthine, 1-methylxanthine, theophylline, theobromine, derivatives thereof, and mixtures thereof. Accordingly, the composition may include from about 0.1 wt % to about 10 wt % of the xanthine compound, from about 0.5 wt % to about 5 wt % of the xanthine compound, or from about 1 wt % to about 2 wt % of the xanthine compound, for example, wherein the wt % is based on the total weight of the hair care composition. For example, the hair care composition may further include about 0.75 wt % of caffeine.

4. Vitamin $B_3$ Compounds

The hair care compositions can further include a vitamin $B_3$ compound. As used herein, "vitamin $B_3$ compound" means nicotinic acid, niacinamide, nicotinyl alcohol, derivatives thereof, and mixtures thereof. The vitamin $B_3$ compound may be included as the substantially pure material, or as an extract obtained by suitable physical and/or chemical isolation from natural (e.g., plant) sources. Accordingly, the composition may include from about 0.1 wt % to about 25 wt % of the vitamin $B_3$ compound; from about 0.5 wt % to about 15 wt % of the vitamin $B_3$ compound; or from about 3.5 wt % to about 7.5 wt % of the vitamin $B_3$ compound, for example, wherein the wt % is based on the total weight of the hair care composition. For example, the hair care composition may further include about 2.5 wt % of vitamin $B_3$.

5. Panthenol Compounds

The hair care compositions can further comprise a panthenol compound. As used herein, the term "panthenol compound" includes panthenol, one or more pantothenic acid derivatives, and mixtures thereof. Non-limiting examples of panthenol compounds include D-panthenol ([R]-2,4-dihydroxy-N-[3-hydroxypropyl)]-3,3-dimethylbutamide), D,L-panthenol, pantothenic acids and their salts (e.g., the calcium salt), panthenyl triacetate, royal jelly, panthetine, pantotheine, panthenyl ethyl ether, pangamic acid, pantoyl lactose, Vitamin B complex, or mixtures thereof. Accordingly, the composition may include from about 0.01 wt % to about 5 wt % of the panthenol compound; from about 0.03 wt % to about 3 wt % of the panthenol compound; from about 0.05 wt % to about 2 wt % of the panthenol compound; or from about 0.1 wt % to about 1 wt % of the panthenol compound, for example, wherein the wt % is based on the total weight of the hair care composition. For example, the hair care composition may further include about 0.15 wt % of panthenol.

The compositions may include other common hair ingredients such as anti-dandruff actives such as pyrithione zinc, minoxidil, silicones, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

6. Anti-Dandruff Actives

The hair care compositions can further include an anti-dandruff active. Suitable, non-limiting examples of anti-dandruff active include: antimicrobial actives, pyridinethione salts; azoles, such as ketoconazole, climbasole, econazole, and elubiol; selenium sulphide; particulate sulfur; keratolytic agents such as salicylic acid; and mixtures thereof. In an embodiment, an anti-dandruff particulate is a pyridinethione salt. Such anti-dandruff particulate should be physically and chemically compatible with the components of the composition, and should not otherwise unduly impair product stability, aesthetics, or performance.

Pyridinethione particulates are suitable particulate anti-dandruff actives for use in hair care compositions of the present invention. In an embodiment, the anti-dandruff active is a 1-hydroxy-2-pyridinethione salt and is in particulate form. In an embodiment, the concentration of pyridinethione anti-dandruff particulate ranges from about 0.01 wt % to about 5 wt %, or from about 0.1 wt % to about 3 wt %, or from about 0.1 wt % to about 2 wt %, by weight of the hair care composition. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809, 971; 3,236,733; 3,753,196; 3,761,418; 4,345,080; 4,323, 683; 4,379,753; and 4,470,982.

In an embodiment, in addition to the anti-dandruff active selected from polyvalent metal salts of pyrithione, the composition can further include one or more anti-fungal and/or anti-microbial actives. In an embodiment, the anti-microbial active is selected from the group consisting of: coal tar, sulfur, charcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof.

In an embodiment, the azole anti-microbials is an imidazole selected from the group consisting of benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of terconazole, itraconazole, and mixtures thereof. When present in the composition, the azole anti-microbial active is included in an amount of from about 0.01 wt % to about 5 wt %, or from about 0.1 wt % to about 3 wt %, or from about 0.3 wt % to about 2 wt %, wherein the wt % is based on the total weight of the hair care composition.

The present invention can further include a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the hair care composition can further include an effective amount of a zinc-containing layered material. In an embodiment, the hair care composition comprises from about 0.001 wt % to about 10 wt %, or from about 0.01 wt % to about 7 wt %, or from about 0.1 wt % to about 5 wt % of a zinc-containing layered material, wherein the wt % is based on the total weight of the hair care composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_{x}(OH)_2]^{x+}A^{m-}_{x/m}\cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^{+}A^{n-}_{(1=3y)/n}\cdot nH_2O$ where the two metal ions ($M^{2+}$) may be the same or different. If they are the same and represented by zinc, the formula simplifies to $[Zn_{1+x}(OH)_2]^{2x+}2xA^{-}\cdot H_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition can further include basic zinc carbonate. Commercially available sources of basic zinc carbonate include zinc Carbonate Basic (Cater Chemicals: Bensenville, Ill., USA), zinc Carbonate (Shepherd Chemicals: Norwood, Ohio, USA), Zinc Carbonate (CPS Union Corp.: New York, N.Y., USA), zinc Carbonate (Elementis Pigments: Durham, UK), and zinc Carbonate AC (Bruggemann Chemical: Newtown Square, Pa., USA). Basic zinc carbonate, which also may be referred to commercially as "zinc carbonate" or "zinc carbonate basic" or "zinc hydroxy carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

In one embodiment, the hair care composition further comprises a rheology modifier to increase the substantivity of the composition, such that it does not drip undesirably onto other areas of the body, onto clothing, or onto home furnishings and may also perform as a film former, thereby increasing the delivery of hair anti-aging agents to the hair follicle and surrounding tissue. Any suitable rheology modifier can be used, for example, a cellulose-based rheology modifier, such as hydroxypropylmethylcellulose. Other non-limiting examples of rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (ME-HEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and combinations thereof.

According to yet another embodiment, the hair care composition may further include one or more solvents, such as dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, and 1,6-hexanediol, or combinations thereof.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the embodiments of the present invention may be hair tonics, leave-on hair products such as conditioners, treatment, and styling products, rinse-off hair products such as conditioners, shampoos, and treatment products; and any other form that may be applied to the scalp.

The hair care compositions are generally prepared by conventional methods such as are known in the art of making topical compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

II. Method for Increasing the Appearance of Thicker and Fuller Hair and/or Delaying the Appearance of Gray Hair According to yet another embodiment of the present invention, a method is provided for increasing the diameter of the hair shaft and follicle; increasing the density of hair follicles; and/or delaying the appearance of gray hair. This may lead to an appearance of thicker and/or fuller hair and may lead to the appearance of delayed onset of gray hair. In one aspect, the method comprises applying the hair care composition to a skin surface from which a region of hair grows. For instance, the hair care composition can be applied to the scalp. In another embodiment, the method comprises topically applying a hair care composition comprising an effective amount of hair anti-aging agents to a region of skin of a mammal seeking to increase the appearance of thicker and/or fuller hair or delaying the appearance of gray hair.

In still another embodiment, the method comprises applying the composition according to a regimen, wherein said regimen comprises:

(a) cleansing the scalp to form a cleansed scalp;
(b) topically applying the composition to said cleansed scalp.

The hair care composition may be used daily, weekly, or in a variety of regimens. The hair care composition may be used more than once a day, such as at night and in the morning. The product may be used after washing the hair (also on wet or dry hair), which may mean using the composition more than once per day on certain days or use only a few times per week. The hair care composition may be used three times per day, twice per day, once per day, six times per week, five times per week, four times per week, three times per week, two times per week, or one time per week. In some embodiments, the hair care composition is used four, five, six or seven times per week.

According to another embodiment, the hair care composition is applied to at least once a day for at least about four weeks, or at least twice a day for at least about four weeks.

According to another embodiment, the hair care composition is applied at least once a day for at least about eight weeks.

The hair care composition may be used by males and females. The hair care composition may be desired to be used by individuals who desire to promote hair growth or have healthier or younger looking hair. For example, the hair care composition may be used on subjects who have no diagnosed hair loss. The hair care composition may be used on subjects having an age of greater than about 20, 25, 30, 35, 40, 45, or 50. The hair care composition may be used on subjects having an age of less than about 70, 65, 60, 55, or 50. Accordingly, the hair care composition may be used on subjects between the ages of about 20-70, from about 30-60, and from about 35-55. Hair diameter may start to decrease after age 20 so healthier hair and increased appearance of fuller and thicker hair may be desired after these ages. Hair diameter continues to decrease and in some subject to a greater extent after age 30 or 40. Additionally, gray hair begins to emerge as early as age 20 but more commonly after age 30 or 40 depending upon genetics.

Formulations and Examples

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

TABLE 1

Exemplary formulations

| | Ingredients | Supplier | Role | Concentrations formulated | Possible Ranges |
|---|---|---|---|---|---|
| 1 | Ethanol | Equistar Chemicals Lp | alcohol/solvent | 20%, 21%, 50%, 57%, 70% | 20-75% |
| 2 | Water | Crystal Springs | carrier | QS | QS |
| 3 | Tween 80 | Lonza Inc | nonionic surfactant | 0%, 2.5%, 5%, 10% | 0-10% |
| 4 | Hydrolite-5 | Symrise Inc | alcohol/solvent | 0%, 2.5%, 5%, 10% | 0-10% |
| 5 | Dipropylene Glycol (DPG) | Dow Chemical Co | alcohol/solvent | 0%, 5%, 50% | 0-50% |
| 6 | Arlasolve DMI (dimethyl isosorbide) | Croda Inc | high purity solvent | 0%, 8% | 0-8% |
| 9 | Citric Acid | Archer Daniels Midland | Neutralizer | 0-3% | <3% |
| 12 | SF 1202 Silicone fluid | Dow Corning | moisturizer | 19% | 1-20% |
| 13 | PEG 10 Dimethicone | Momentive | moisturizer | 1% | 0.5-5% |
| | Silsoft 430 | | | | 0.5-5% |
| | Camellia Plant Fraction | IBT | Anti-aging agent | 0.1%, 1%, 10%, 20% | 0.05-30% |
| | Fevefew Plant Fraction | IBT | Anti-aging agent | 0.1%, 1%, 10%, 20% | 0.05-30% |
| | Parsely Plant Fraction | IBT | Anti-aging agent | 0.1%, 1%, 10%, 20% | 0.05-30% |
| | Kelp Plant Fraction | IBT | Anti-aging agent | 0.1%, 1%, 10%, 20% | 0.05-30% |
| 14 | Vitamin E Acetate | BASF | skin penetration enhancement, moisturizer | 0.50% | 0.5- 5% |

TABLE 1-continued

Exemplary formulations

| Ingredients | Supplier | Role | Concentrations formulated | Possible Ranges |
|---|---|---|---|---|
| 15 Hexylene Glycol | John R Hess & Co Inc | skin penetration enhancement | 5% | 0.5-10% |
| 16 Oleic Acid | Peter Cremer NA Lp | skin penetration enhancement | 1% | 0.5-3% |
| 17 Panthenol | DSM Nutr. Products | conditioning agent | 0.15% | 0.1-1% |
| 18 Niacinamide | DSM Nutr. Products | conditioning agent | 2.50% | 0.5-5% |
| 19 Caffeine | BASF Pharmachemikalien | conditioning agent | 0.75% | 0.5-5% |
| 20 Wakana HE | GIVAUDAN | Fragrance | 1% | 0.2-2% |
| 21 ACULYN™ 28 or CARBOPOL® U21 | Dow Chemical Lubrizol | rheology modifier | 1.25%, 2.50%, 3.75%, 5.00%, 7.50%, 10.00%, 12.50%, 17.50% | 0.10-17.50% |

General Procedure: The hair care compositions may be prepared to methods commonly used by those skilled in the art. For example, a thickening agent (e.g., a polymer such as carbopol) may be added to water under agitation sufficient to affect complete mixing without substantially aerating the solution. Continue mixing until the thickening agent is fully hydrated before adding additionally ingredients. Add additional dermatologically acceptable carriers, followed by the serum fractions and continue mixing until a homogenous solution is achieved. Measure pH and adjust if desired (e.g., 5.5 to 7).

Formula 1: 5.00% FeverFew and *Camellia* serum fraction blend (30/70) formulation

| Ingredient | Lot | % Added | Weight (g) |
|---|---|---|---|
| Water | | 33.35 | 33.35 |
| U21 | | 0.35 | 0.35 |
| Ethanol | | 50.00 | 50.00 |
| Fraction: FeverFew & *Camellia* (30/70) | B02-0712M/OS-0562 | 5.00 | 5.00 |
| Silsoft 430 | | 1.00 | 1.00 |
| Perfume Watergarden Craft 2 | | 0.30 | 0.30 |
| Water | | 10.00 | 10.00 |
| Total | | 100.00 | 100.00 |

Formula 2: 5.00% FeverFew and *Camellia* serum fraction blend (30/70) formulation.

| Ingredient | Lot | % Added | Weight (g) |
|---|---|---|---|
| Water | | 26.50 | 26.50 |
| A28 | | 7.50 | 7.50 |
| Ethanol | | 50.00 | 50.00 |
| Fraction: FeverFew & *Camellia* (30/70) | B02-0712M/OS-0562 | 5.00 | 5.00 |
| Perfume Wakana HE | | 1.00 | 1.00 |
| Water | | 10.00 | 10.00 |
| Total | | 100.00 | 100.00 |

Formula 3: 5.00% Kelp and Parsley serum fraction blend (50/50) formulation.

| Ingredient | Lot | % Added | Weight (g) |
|---|---|---|---|
| Water | | 33.35 | 33.35 |
| U21 | | 0.35 | 0.35 |
| Ethanol | | 50.00 | 50.00 |
| Fraction: Kelp & Parsley (50/50) | B19-0712M/OS-0563 | 5.00 | 5.00 |
| Silsoft 430 | | 1.00 | 1.00 |
| Perfume Watergarden Craft 2 | | 0.30 | 0.30 |
| Water | | 10.00 | 10.00 |
| Total | | 100.00 | 100.00 |

Formula 4: 5.00% Kelp and Parsley serum fraction blend (50/50) formulation.

| Ingredient | Lot | % Added | Weight (g) |
|---|---|---|---|
| Water | | 26.50 | 26.50 |
| A28 | | 7.50 | 7.50 |
| Ethanol | | 50.00 | 50.00 |
| Fraction: Kelp & Parsley (50/50) | B19-0712M/OS-0563 | 5.00 | 5.00 |
| Perfume Wakana HE | | 1.00 | 1.00 |
| Water | | 10.00 | 10.00 |
| Total | | 100.00 | 100.00 |

III. Bio-Activity

Briefly, as is commonly known by those skilled in the art of the instant disclosure, the hair cycle consists of three phases. The first phase, or growth phase, is known as anagen and lasts, on average, between three and four years. The second phase consists of discontinued growth over a period of two to three weeks. This phase is called catagen. The last phase, called telogen, is the phase where the hair falls out. This phase occurs fairly slowly, over the course of three to four months, as the bulbar zone of the hair follicle regresses and the hair shaft detaches and is expulsed towards the surface of the skin.

In accord with one embodiment of the present invention, a hair care composition comprising a first combination of the *camellia* serum fraction and the feverfew serum fraction,- and/or the parsley serum fraction and the kelp serum fraction, is applied to the scalp and/or the base of the hair on the scalp, to increase the appearance of healthier and younger-looking hair. A topical application of one or more hair growth stimulating agents to regions where the appearance of more hair is desired may actually improve the appearance of the region by having an appearance of thicker and/or fuller hair and/or delay the appearance of gray hair.

Although not wishing to be limited by theory, it is believed that topical application of various hair anti-aging agents can: (1) interrupt or inhibit an inflammatory cycle at the hair follicles, which in turn may extend the anagen phase of the follicles; and/or (2) stimulate the production of melanin in hair melanocytes, which in turn may delay the emergence of gray hair. Accordingly, the topical application of the hair care compositions may also help to slow the rate in which hair leaves the anagen phase, delay the appearance of gray hair, or both. Furthermore, the topical application can lead to the appearance of younger looking hair, since hair diameter is known to decrease with one's chronological age and the appearance of gray hair can be delayed.

The topical application of the hair care composition of can aid in lengthening the anagen phase. The lengthening of the anagen phase can be achieved by either blocking the transition from anagen phase to telogen phase or by inhibiting the transition from anagen phase to telogen phase. The hair follicles are in a growing phase (anagen) or in a resting phase (telogen). Follicles are predominately in the anagen phase. The anagen phase may typically last for approximately 2 to 10 years, with an average duration of about 3 to 4 years that can vary depending on a variety of factors. Conversely, the telogen phase is much shorter and may typically last for about 3 to 4 months. In general, a person will have approximately 94% of the follicles in anagen phase and 6% of the follicles in telogen phase. Each month approximately 2% of the follicles leave anagen phase and transition to telogen phase and at the same time approximately 2% of the follicles leave telogen phase and transition to anagen phase. With the application of the hair care compositions of the present invention, the approximately 2% of the follicles leaving anagen phase can be either blocked or delayed resulting in an increased percent of hair follicles in anagen phase. The increase in the amount of follicles in anagen phase increases the hair density on the head. It is believed that the length of the anagen phase can be increased from about 2 weeks to about 2.5 months. The increase in hair density (number of hair on a certain area of the scalp) can be measured.

Two methods for predicting the efficacy of the serum fraction combinations to affect the inflammatory cycle at the hair follicles is using in vitro bio-assays. More specifically, interleukin signaling inhibition via interleukin-1 receptor-associated kinase (IRAK-4) inhibition is the predictive bio-assay method described below.

Interleukin-1 Signaling Inhibition: Interleukin-1 (IL-1) is a family of pro-inflammatory cytokines that initiate biochemical signaling pathways to increase inflammation. In the hair follicles, IL-1 is an endogenous factor that drives the switch from anagen to catagen, the transition phase that precedes telogen. It is believed that inhibition of IL-1 signaling at any point within its pathways will prolong the anagen phase by the block or delay of the switch of hair follicles from the anagen phase to the catagen phase.

Interleukin-1 Receptor-Associated Kinase Inhibition: Interleukin-1 receptor-associated kinase (IRAK-4) is an integral mediator of IL-1 signaling that recruits other kinases upon IL-1 stimulation for subsequent signal transduction. The inhibition of IRAK-4 activity is measured by the amount of ATP using the ADP-Glo™ kinase kit (Promega) after incubation of the full-length human recombinant IRAK-4 enzyme system (Promega) with inhibitors for 30 minutes. The ADP-Glo™ kit was used in accordance with the manufacturer's instructions.

Melanin Synthesis Activation: Melanin is the pigment made by melanocytes that is responsible for both hair and skin color. Melanin synthesis only occurs during the anagen phase. Prolonging the anagen phase potentially prolongs basal melanin synthesis and also provides the opportunity to increase the synthesis of melanin with specific activators. The activation of melanin is measured in an in vitro model of B16-F1 melanocytes (ATCC) in culture. Melanocytes are incubated with activators for 48 hours and the melanin formed is measured by reading the optical density (O.D.) at 410 nm on a spectrophotometer.

Melanin Synthesis Activation Materials: Plates: Corning® 96 Well Flat Clear Bottom White Polystyrene TC-Treated Microplates, #3903; Cells: B16-F1 (ATCC); Growing Medium: DMEM, Gibco Invitrogen, #11965-092 with 10% FBS and 1% Penicillin/strep/Glutamine (GLBCO cat#15701); serum fractions and blends; preservatives; and controls.

Melanin Synthesis Activation Method: Day 1: Seeding B16-F1 cells, 2000/well/100 ul; Day 2: Treating the compounds by adding 10 μl of diluted compounds into each well; and Day 4: Measure the color change in each well. Checking the cell viability under microscope, if cell confluence is <50%, the data for this point is not used. Measuring OD value (melanin product) at Vis/UV reader, 410 nM after adding 100 μl of 1% NaOH (1 ml 50% NaOH+49 ml H2O) into each well. Note: Due to prevalence of color with serum fractions, wells with media but no cells were also treated and used as color control blanks to remove over-estimation due to serum color.

Statistical Significance Definition: One-tailed 2-sample t-tests were conducted. Statistical significance is defined as $p<0.05$. Examples in this application are provided with values of $p<0.01$. Statistically significant and synergistic blends are defined as blends with statistically significantly greater activity than that of both individual serum fraction components.

A. Kelp and Parsley Serum Fractions (1) The kelp serum fraction, the parsley fraction, and combinations can be assessed for melanin synthesis action (all serum fractions analyzed at 1% (v/v) of the analytical composition):

TABLE 1

Example 1A: Kelp-Parsley 10:90 Blend
K: Lot# MP0726M/MS-0571; P: Lot #PA1117L/HP-0570;
K + P: Lot #: B19-0729M/OS-0572

| Serum Fraction (1%) | Fold activation | 2-sample t-test vs. blend ($p < 0.01$ statistically significant) |
|---|---|---|
| Kelp | 1.62 | 0.000008 |
| Parsley | 1.91 | 0.000010 |
| Kelp-Parsley 10:90 Blend | 6.36 | |

TABLE 2

Example 1B: Kelp-Parsley 20:80 Blend
K: Lot# MP0726M/MS-0571;
P: Lot #PA1117L/HP-0570; K + P: Lot #: B19-0729M/OS-0573

| Serum Fraction (1%) | Fold activation | 2-sample t-test vs. blend ($p < 0.01$ statistically significant) |
|---|---|---|
| Kelp | 1.62 | 0.000016 |
| Parsley | 1.91 | 0.000022 |
| Kelp-Parsley 20:80 Blend | 4.25 | |

TABLE 3

Example 1C: Kelp-Parsley 30:70 Blend
K: Lot# MP0726M/MS-0571;
P: Lot #PA1117L/HP-0570; K + P: Lot #: B19-0729M/OS-0574

| Serum Fraction (1%) | Fold activation | 2-sample t-test vs. blend ($p < 0.01$ statistically significant) |
|---|---|---|
| Kelp | 1.62 | 0.001324 |
| Parsley | 1.91 | 0.004537 |
| Kelp-Parsley 30:70 Blend | 2.66 | |

TABLE 4

Example 1D: Kelp-Parsley 40:60 Blend
K: Lot# MP0726M/MS-0571;
P: Lot #PA1117L/HP-0570; K + P: Lot #: B19-0729M/OS-0575

| Serum Fraction (1%) | Fold activation | 2-sample t-test vs. blend ($p < 0.01$ statistically significant) |
|---|---|---|
| Kelp | 1.62 | 0.000004 |
| Parsley | 1.91 | 0.000005 |
| Kelp-Parsley 40:60 Blend | 4.37 | |

TABLE 5

Example 1E: Kelp-Parsley 50:50 Blend
K: Lot# MP0726M/MS-0571;
P: Lot #PA1117L/HP-0570; K + P: Lot #: B19-0729M/OS-0576

| Serum Fraction (1%) | Fold activation | 2-sample t-test vs. blend ($p < 0.01$ statistically significant) |
|---|---|---|
| Kelp | 1.62 | 0.000571 |
| Parsley | 1.91 | 0.001749 |
| Kelp-Parsley 50:50 Blend | 2.77 | |

TABLE 6

Example 1F: Kelp-Parsley 70:30 Blend
K: Lot# MP0726M/MS-0571;
P: Lot #PA1117L/HP-0570; K + P: Lot #: B19-0729M/OS-0578

| Serum Fraction (1%) | Fold activation | 2-sample t-test vs. blend ($p < 0.01$ statistically significant) |
|---|---|---|
| Kelp | 1.62 | 0.001198 |
| Parsley | 1.91 | 0.004543 |
| Kelp-Parsley 70:30 Blend | 2.61 | |

TABLE 7

Example 1G: Kelp-Parsley 50:50 Blend
K: Lot# 0320J/MS-0363;
P:Lot #PA1117L/HP-0499; K + P: Lot #: B19-0215M/OS-0529

| Serum Fraction (1%) | Fold activation | 2-sample t-test vs. blend ($p < 0.01$ statistically significant) |
|---|---|---|
| Kelp | 2.13 | 0.000007 |
| Parsley | 1.41 | 0.000007 |
| Kelp-Parsley 50:50 Blend | 6.7 | |

A constant concentration is used to directly demonstrate that the same level of the dry matter content of the blended serum fraction has significantly more activity than the level of either of the individual serum fractions alone. This demonstrates that the two serums in the blend work synergistically together to afford significantly better biological activity. For example in Example 1A, the individual serum fractions of kelp and parsley at 1% give % give 1.62 and 1.91 fold activation but 1% of a 10:90 blend of these individual serum fractions give a significantly and much greater activation of 6.36 fold.

(2) The combination of kelp serum fraction and the parsley serum fraction can be assessed for IRAK-4 inhibition (all serum fractions analyzed at 4% (v/v) of the analytical composition):

TABLE 8

Example 1H: Kelp-Parsley 50:50 Blend
K: Lot# MP0726M/MS-0571;
P: Lot #PA1117L/HP-0570; K + P: Lot #: B19-0729M/OS-0576

| Serum Fraction (4%) | % inhibition | 2-sample t-test vs. blend ($p < 0.01$ statistically significant) |
|---|---|---|
| Kelp | 67.7 | 0.001127 |
| Parsley | 43 | 0.000034 |
| Kelp-Parsley 50:50 Blend | 76.3 | |

TABLE 9

Example 1I: Kelp-Parsley 60:40 Blend
K: Lot# MP0726M/MS-0571;
P: Lot #PA1117L/HP-0570; K + P: Lot #: B19-0729M/OS-0577

| Serum Fraction (4%) | % inhibition | 2-sample t-test vs. blend ($p < 0.01$ statistically significant) |
|---|---|---|
| Kelp | 67.7 | 0.000015 |
| Parsley | 43 | 0.000012 |
| Kelp-Parsley 60:40 Blend | 77.7 | |

TABLE 10

Example 1J: Kelp-Parsley 70:30 Blend
K: Lot# MP0726M/MS-0571;
P: Lot #PA1117L/HP-0570; K + P: Lot #: B19-0729M/OS-0578

| Serum Fraction (4%) | % inhibition | 2-sample t-test vs. blend ($p < 0.01$ statistically significant) |
|---|---|---|
| Kelp | 67.7 | 0.000336 |
| Parsley | 43 | 0.000022 |
| Kelp-Parsley 70:30 Blend | 76.7 | |

TABLE 11

Example 1K: Kelp-Parsley 80:20 Blend
K: Lot# MP0726M/MS-0571;
P: Lot #PA1117L/HP-0570; K + P: Lot #: B19-0729M/OS-0579

| Serum Fraction (4%) | % inhibition | 2-sample t-test vs. blend ($p < 0.01$ statistically significant) |
|---|---|---|
| Kelp | 67.7 | 0.001445 |
| Parsley | 43 | 0.000030 |
| Kelp-Parsley 80:20 Blend | 72 | |

A constant concentration was used to directly demonstrate that the same level of dry weight matter in the blended serum fraction has significantly more activity than the level of either of the individual serum fractions alone. This shows that the two serums in the blend work synergistically together to afford significantly better biological activity. For example in Table 11, Experiment 1K, the individual serum fractions of kelp and parsley at 4.0% give 67.7% and 43% inhibition respectively, whereas 4.0% of a 50:50 blend of these serum fractions gives a significantly greater inhibition of 76.3%.

B. *Camellia* and Feverfew Serum Fractions (1) The *camellia* serum fraction, the feverfew fraction, and combinations can be assessed for melanin synthesis action (all serum fractions analyzed at 0.8% (v/v) of the analytical composition):

TABLE 12

Example 2A: *Camellia*-Feverfew 50:50 Blend
C: Lot#TECJ062904-0161-01;
F: Lot#FF0811K/TL; C + F: Lot#B02-0712M/OS-0561

| Serum Fraction (1%) | Fold activation | 2-sample t-test vs. blend ($p < 0.01$ statistically significant) |
|---|---|---|
| *Camellia* | 2.26 | 0.003412 |
| Feverfew | 1.72 | 0.000648 |
| *Camellia*-Feverfew 50:50 Blend | 3.24 | |

TABLE 13

Example 2B: *Camellia*-Feverfew 80:20 Blend
C: Lot#TECJ062904-0161-01;
F: Lot#FF0811K/TL; C + F: Lot#B02-0719M/OS-0567

| Serum Fraction (1%) | Fold activation | 2-sample t-test vs. blend ($p < 0.01$ statistically significant) |
|---|---|---|
| *Camellia* | 2.26 | 0.000309 |
| Feverfew | 1.72 | 0.000088 |
| *Camellia*-Feverfew 80:20 Blend | 3.73 | |

TABLE 14

Example 2C: *Camellia*-Feverfew 20:80 Blend
C: Lot#TECJ062904-0184;
F: Lot#FF0811K/TL; C + F: Lot#FFCSWASC02P-0351

| Serum Fraction (1%) | Fold activation | 2-sample t-test vs. blend ($p < 0.01$ statistically significant) |
|---|---|---|
| *Camellia* | 2.26 | 0.000041 |
| Feverfew | 2.02 | 0.000003 |
| *Camellia*-Feverfew 20:80 Blend | 5.02 | |

A constant concentration is used to directly demonstrate that the same level of the dry weight matter in the blended serum fraction has significantly more activity than the level of either of the individual serum fractions alone. This demonstrates that the two dry weight matters in the blend work synergistically together to afford significantly better biological activity. For example in Table 14, Experiment 2C, the individual serum fractions of *camellia* and feverfew at 1% give 2.26 and 2.02 fold activation respectively, whereas 1% of a 20:80 blend of these serum fractions give a significantly and much greater activation of 5.02 fold. The same is demonstrated for a 50:50 blend (Table 12, Experiment 2A) and 80:20 blend (Table 13, Experiment 2B).

(2) The *camellia* serum fraction, the feverfew fraction, and combinations can be assessed for IRAK-4 inhibition (all serum fractions analyzed at 0.8% (v/v) of the analytical composition):

TABLE 15

Example 2D: *Camellia*-Feverfew 50:50 Blend
C: Lot#TECJ062904-0161-01;
F: Lot#FF0811K/TL; C + F: Lot#B02-0712M/OS-0561

| Serum Fraction (0.8%) | % inhibition | 2-sample t-test vs. blend ($p < 0.01$ statistically significant) |
|---|---|---|
| *Camellia* | 8 | 0.000604 |
| Feverfew | 9 | 0.000502 |
| *Camellia*-Feverfew 50:50 Blend | 37.7 | |

TABLE 16

Example 2E: *Camellia*-Feverfew 80:20 Blend
C: Lot#TECJ062904-0161-01;
F: Lot#FF0811K/TL; C + F: Lot#B02-0719M/OS-0567

| Serum Fraction (0.8%) | % inhibition | 2-sample t-test vs. blend ($p < 0.01$ statistically significant) |
|---|---|---|
| *Camellia* | 8 | 0.000045 |
| Feverfew | 9 | 0.000029 |
| *Camellia*-Feverfew 80:20 Blend | 54.3 | |

A constant concentration is used to directly demonstrate that the same level of the dry weight matter in the blended serum fraction has significantly more activity than the level of either of the individual serum fractions alone. This demonstrates that the two serums in the blend work synergistically together to afford significantly better biological activity. For example in Table 16, Example 2E, the individual serum fractions of *camellia* and feverfew at 0.8% give 8% and 9% inhibition respectively, whereas 0.8% of a 80:20 blend of these serum fractions gives a significantly and much greater inhibition of 54.3%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A bioactive composition for activating melanin comprising:
   a. an effective amount of a bioactive blend selected from:
      i. a first composition comprising a combination of a *camellia* serum fraction and a feverfew serum fraction in a weight ratio of about 10:90 to about 90:10; and/or
      ii. a second composition comprising a combination of a parsley serum fraction and a kelp serum fraction in a weight ratio of about 10:90 to about 90:10; and optionally
   b. a dermatologically acceptable carrier.

2. The bioactive composition of claim 1, wherein the weight ratio of the *camellia* serum fraction to the feverfew serum fraction is from about 20:80 to about 80:20.

3. The bioactive composition of claim 1, wherein the weight ratio of the *camellia* serum fraction to the feverfew serum fraction is about 50:50 to about 80:20.

4. The bioactive composition of claim 1, further comprising a thickening agent.

5. The bioactive composition of claim 1, wherein the weight ratio of the parsley serum fraction to the kelp serum fraction is from about 30:70 to about 70:30.

6. The bioactive composition of claim 1, wherein the weight ratio of the parsley serum fraction to the kelp serum fraction is about 50:50.

7. The bioactive composition of claim 1, wherein said bioactive composition comprises a combination of the first composition and the second composition.

8. The bioactive composition of claim 1, wherein said bioactive composition possesses one or more of the following properties: anti-aging, antioxidant and/or free radical scavenging, inhibition of enzymes associated with skin aging and environmental damage, skin protection, repair of human tissue or skin, UV protection, and protection from ozone and/or osmotic shock.

9. The bioactive composition of claim 1, wherein said bioactive composition has hair and/or skin anti-aging activity.

* * * * *